United States Patent [19] [11] 4,004,032
Schromm et al. [45] Jan. 18, 1977

[54] PHARMACEUTICAL COMPOSITIONS CONTAINING A 1-(3-TRIFLUOROMETHYL-4'-CHLORO-PHENYL)-2-(CARBOXYLIC ACYLAKYL-AMINO) PROPANE AND METHOD OF USE

[75] Inventors: Kurt Schromm; Ernst-Otto Renth; Anton Mentrup; Richard Reichl, all of Ingelheim am Rhein, Germany

[73] Assignee: Boehringer Ingelheim GmbH, Ingelheim am Rhein, Germany

[22] Filed: Jan. 27, 1976

[21] Appl. No.: 652,801

Related U.S. Application Data

[60] Division of Ser. No. 478,264, June 11, 1974, Pat. No. 3,950,335, which is a continuation-in-part of Ser. No. 138,002, April 27, 1971, abandoned.

[30] Foreign Application Priority Data

May 2, 1970 Germany ............................ 2021620

[52] U.S. Cl. .............................................. 424/330
[51] Int. Cl.² ...................................... A61K 31/135
[58] Field of Search .................................. 424/330

[56] References Cited

UNITED STATES PATENTS 3,459,803  8/1969  Faust et al. ...................... 424/330
3,515,741  6/1970  Thoma et al. .................... 424/330

Primary Examiner—Sam Rosen
Attorney, Agent, or Firm—Hammond & Littell

[57] ABSTRACT

Pharmaceutical dosage unit compositions containing as an active ingredient a racemic or optically active compound of the formula

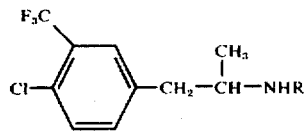

wherein R is $-(CH_2)_n-CO-C_6H_5$ or $-(CH_2)_n-CO-CH_3$, $n$ is 1 or 2, or a non-toxic, pharmacologically acceptable acid addition salt thereof; and a method of using the same as appetite suppressants.

8 Claims, No Drawings

PHARMACEUTICAL COMPOSITIONS CONTAINING A 1-(3-TRIFLUOROMETHYL-4'-CHLORO-PHENYL)-2-(CARBOXYLIC ACYLAKYL-AMINO) PROPANE AND METHOD OF USE

This is a division of copending application Ser. No. 478,264 filed June 11, 1974, now U.S. Pat. No. 3,950,335 which is a continuation-in-part of application Ser. No. 138,002, now abandoned.

This invention relates to novel pharmaceutical compositions containing a 1-(3'-trifluoromethyl-4'-chloro-phenyl)-2-(carboxylic acylalkyl-amino)-propane, as well as to a method of using the same as appetite suppressants.

More particularly, the present invention relates to pharmaceutical dosage unit compositions containing as an active ingredient a racemic or optically active compound

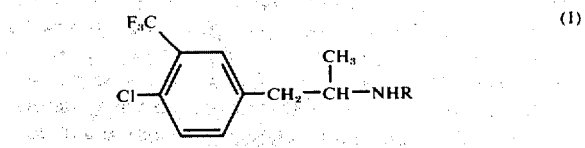

wherein
R is $-(CH_2)_n-CO-C_6H_5$ or $-(CH_2)_n-CO-CH_3$,
n is 1 or 2, or a non-toxic, pharmacologically acceptable acid addition salt thereof.

The compounds of the formula I may be prepared by treating a compound of the formula

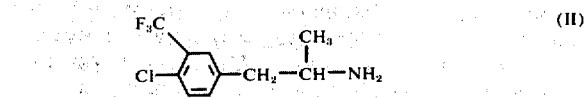

with an alkylating agent of the formula

in which R has the meanings defined above and Y is a radical which may be split off as an anion, for example a halogen atom or the radical of a suitable sulfonic acid, such as toluene-or methanesulfonic acid. If R is $-(CH_2)_2-CO-C_6H_5$ or $-(CH_2)_2-CO-CH_3$, this substituent may be introduced under the conditions of the Mannich-reaction.

Racemic mixtures of a compound of the formula I may, if desired, be resolved into optically active components thereof by conventional methods, such as by fractional precipitation with an optically active acid, followed by liberation of the optionally active base.

The compounds embraced by formula 1, in the racemic as well as optically active forms, are organic bases and therefore form acid addition salts with inorganic or organic acids by known methods. Examples of non-toxic, pharmacologically acceptable acid addition salts are those formed with hydrochloric acid, sulfuric acid, phosphoric acid, tartaric acid, ascorbic acid 8-chloro-theophylline or the like.

The starting compounds may be prepared by conventional processes, or in analogous fashion, as illustrated by the reaction sequence below.

Thus, condensation of a substituted benzaldehyde (IV) with nitroethane yields a nitro-olefin of the formula V, from which an amine of the formula II is obtained by reduction with a complex metal hydride, such as lithium aluminum hydride:

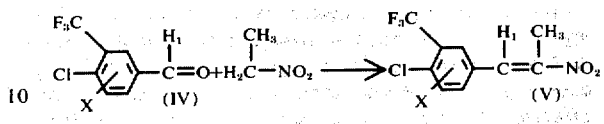

The following examples illustrate the present invention and will enable others skilled in the art to understand it more completely. It should be understood, however, that the invention is not limited solely to the particular examples given below.

EXAMPLE 1

1-(4'-Chloro-3'-trifluoromethyl-phenyl)-2-(phenacyl-amino)-propane and its hydrochloride A mixture consisting of 23.8 gm of 1-(4'-chloro-3'-trifluoromethyl-phenyl)-2-amino-propane, 9.3 gm of -bromo-acetophenone and 100 ml of acetonitrile was stirred for 30 minutes and then evaporated. Ether was added to the residue, the resulting mixture was vacuum-filtered, and the filtrate was evaporated. The residue, 1-(4'-chloro-3'-trifluoromethyl-phenyl)-2-(phenacyl-amino)-propane, was dissolved in acetonitrile, the resulting solution was acidified with ethereal hydrochloric acid, and the precipitate formed thereby was collected and recrystallized from methanol/water, yielding the compound of the formula

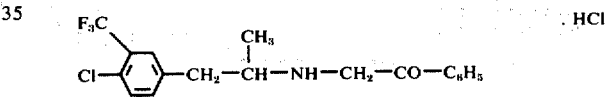

having a melting point of 210°–213° C.

EXAMPLE 2

1-(4'-Chloro-3'-trifluoromethyl-phenyl)-2-(acetonylamino)-propane and its hydrochloride 2.53 ml of chloroacetone were added dropwise to a boiling mixture consisting of 6.45 gm of 1-(4'-chloro-3'-trifluoromethyl-phenyl)-2-amino-propane, 50 ml of acetonitrile and 2.93 gm of sodium carbonate, and the mixture was refluxed for one hour. Thereafter, the reaction mixture was vacuum-filtered, the filtrate was evaporated, and the residue, 1-(4'-chloro-3'-trifluoromethyl-phenyl)-2-(acetonylamino)-propane, was dissolved in ethyl acetate. The resulting solution was acidified with ethereal hydrochloric acid, and then ether was added, and the precipitate formed thereby was collected and recrystallized from isopropanol, yielding the compound of the formula

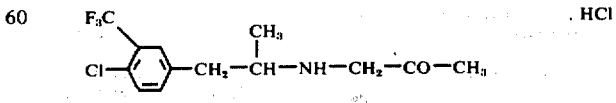

having a melting point of 191°–194° C.

The racemates or optically active compounds embraced by formula I and their non-toxic, pharmacologically acceptable acid addition salts have useful pharmacodynamic properties. More particularly, they exhibit very effective anorectic activities with extremely low central nervous system stimulating side effects and very low toxicity in warm-blooded animals, such as rats.

For pharmaceutical purposes the compounds of the formula I or their non-toxic acid addition salts are administered to warm-blooded animals perorally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups and the like. One effective anorectic dosage unit of the compounds of the formula I or their non-toxic acid addition salts is from 0.0166 to 0.83 mgm/kg body weight, preferably 0.041 to 0.167 mgm/kg body weight.

The following examples illustrate a few oral pharmaceutical dosage unit compositions comprising a compound of the formula I or a non-toxic acid addition salt thereof as an active ingredient and represent the best modes contemplated of putting the invention into practical use. The parts are parts by weight unless otherwise specified.

EXAMPLE 3

Tablets
The tablet composition was compounded from the following ingredients:

| | |
|---|---|
| 1-(4'-chloro-3'-trifluoromethylphenyl)-2-(phenacyl-amino)-propane hydrochloride | 5.0 parts |
| Lactose | 262.0 parts |
| Polyvinylpyrrolidone | 3.0 parts |
| Corn starch | 27.0 parts |
| Colloidal silicic acid | 2.0 parts |
| Magnesium stearate | 1.0 parts |
| Total | 300.0 parts |

Preparation:

The propane compound was intimately admixed with the lactose, the corn starch and the colloidal silicic acid; the resulting mixture was moistened with an aqueous solution of the polyvinylpyrrolidone; the moist mass was granulated by passing it through a 1.5 mm-mesh screen; the granulate was dried at 40° C; the dry granulate was again passed through the screen and was then admixed with the magnesium stearate, and the resulting composition was compressed into 300 mgm-tablets in a conventional tablet-making machine. Each tablet contained 5 mgm of the propane compound and was an oral dosage unit composition with effective anorectic action.

Coated Pills
The pill core composition was compounded from the following ingredients:

| | |
|---|---|
| 1-(4'-Chloro-3'-trifluoromethylphenyl)-2-acetonyl-amino)-propane hydrochloride | 10.0 parts |
| Lactose | 257.0 parts |
| Polyvinylpyrrolidone | 3.0 parts |
| Corn starch | 27.0 parts |
| Colloidal silicic acid | 2.0 parts |
| Magnesium stearate | 1.0 parts |
| Total | 300.0 parts |

Preparation:

The ingredients were compounded as described in Example 3, the finished composition was compressed into 300 mgm-pill cores, and the pill cores were coated in conventional manner with a thin shell consisting essentially of a mixture of sugar, talcum, gum arabic, titanium oxide and polyvinylpyrrolidone. Each coated pill contained 10 mgm of the propane compound and was an oral dosage unit composition with effective anorectic action.

EXAMPLE 5

Wafer Capsules
The capsule filler composition was compounded from the following ingredients:

| | | |
|---|---|---|
| 1-(4'-Chloro-3'-trifluoromethylphenyl)-2-(phenylacyl-amino)-propane hydrochloride | 2.5 | parts |
| Lactose, crystalline | 77.5 | parts |
| Talcum | 20.0 | parts |
| Total | 100.0 | parts |

Preparation:

The phenyl-aminopropane compound was passed through a 0.75 mm-mesh screen and was then intimately and uniformly admixed with the lactose and the talcum, and 100 mgm-portions of the resulting composition were filled into wafer capsules of suitable size. Each capsule contained 2.5 mgm of the phenyl-aminopropane compound and was a peroral dosage unit composition with effective anorectic action.

Analogous results were obtained when any one of the other compounds embraced by formula I or a non-toxic, pharmacologically acceptable acid addition salts thereof was substituted for the particular phenyl-aminopropane in Examples 3 through 5. Likewise, the amount of active ingredient in these illustrative examples may be varied to achieve the dosage unit range set forth above, and the amounts and nature of the inert pharmaceutical carrier ingredients may be varied to meet particular requirements. Moreover, a dosage unit composition according to the present invention may, in addition, contain an effective dosage unit of another type of active ingredient, such as a laxative.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. An anorectic pharmaceutical oral dosage unit composition consisting essentially of an inert pharmaceutical carrier and an effective anorectic amount of a racemic or optically active compound of the formula

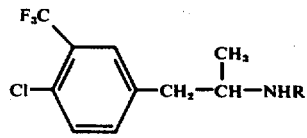

wherein
R is $-(CH_2)_n-CO-C_6H_5$ or $-(CH_2)_n-CO-CH_3$,
n is 1 or 2, or a non-toxic, pharmacologically acceptable acid addition salt thereof.

2. A composition of claim 1, where R is $-CH_2-CO-C_6H_5$ or $-CH_2-CO-CH_3$.

3. A composition of claim 1, where said compound is 1-(4'-chloro-3'-trifluoromethyl-phenyl)-2-(phenacyl-amino)-propane or a non-toxic, pharmacologically acceptable acid addition salt thereof.

4. A composition of claim 1, where said compound is 1-(4'-chloro-3'-trifluoromethyl-phenyl)-2-(acetonyl-amino)-propane or a non-toxic, pharmacologically acceptable acid addition salt thereof.

5. The method of suppressing the appetite of a warm-blooded animal, which comprises perorally administering to said animal an effective anorectic amount of a racemic or optically active compound of the formula

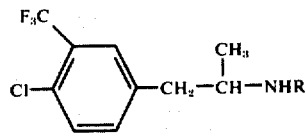

wherein
R is —(CH$_2$)$_n$—CO—C$_6$H$_5$ or —(CH$_2$)$_n$—CO—CH$_3$, n is 1 or 2, or a non-toxic, pharmacologically acceptable acid addition salt thereof.

6. The method of claim 5, where R is —CH$_2$—CO—C$_6$H$_5$ or —CH$_2$—CO—CH$_3$.

7. The method of claim 5, where said compound is 1-(4'-chloro-3'-trifluoromethyl-phenyl)-2-(acetonyl-amino)-propane or a non-toxic, pharmacologically acceptable acid addition salt thereof.

8. The method of claim 5, where said compound is 1-(4'-chloro-3'-trifluoromethyl-phenyl)-2-(phenacyl-amino)-propane or a non-toxic, pharmacologically acceptable acid addition salt thereof.

* * * * *